United States Patent
Pierce et al.

(10) Patent No.: US 10,952,937 B2
(45) Date of Patent: Mar. 23, 2021

(54) ORAL CARE COMPOSITIONS AND DISPENSING SYSTEM THEREFOR

(71) Applicant: Colgate-Palmolive Company, New York, NY (US)

(72) Inventors: Robert Pierce, Basking Ridge, NJ (US); Nagarajan Jayaraman, New York, NY (US)

(73) Assignee: Colgate-Palmolive Company, New York, NY (US)

( * ) Notice: Subject to any disclaimer, the term of this patent is extended or adjusted under 35 U.S.C. 154(b) by 3 days.

(21) Appl. No.: 15/664,692

(22) Filed: Jul. 31, 2017

(65) Prior Publication Data
US 2018/0085292 A1    Mar. 29, 2018

Related U.S. Application Data

(60) Provisional application No. 62/400,878, filed on Sep. 28, 2016.

(51) Int. Cl.
*A61K 8/11*        (2006.01)
*A61K 8/37*        (2006.01)
(Continued)

(52) U.S. Cl.
CPC ............. *A61K 8/11* (2013.01); *A61C 19/066* (2013.01); *A61J 3/07* (2013.01); *A61K 8/022* (2013.01);
(Continued)

(58) Field of Classification Search
CPC .......... A61C 19/066; A61J 3/07; A61K 8/022; A61K 8/11; A61K 8/19; A61K 8/21;
(Continued)

(56) References Cited

U.S. PATENT DOCUMENTS 3,469,521 A * 9/1969 Simjian ................... A47J 31/40
                                                                99/287
3,535,421 A   10/1970 Briner et al.
(Continued)

FOREIGN PATENT DOCUMENTS

| EP | 2111841 | 1/2015 |
| JP | 2008127284 | 6/2008 |
| WO | 2015/111051 | 11/2017 |

OTHER PUBLICATIONS

International Search Report and Written Opinion of the International Searching Authority in International Application PCT/US2017/044666, dated Nov. 21, 2017.
(Continued)

*Primary Examiner* — Kyung S Chang

(57) ABSTRACT

The present disclosure provides a capsule comprising one or more solid oral care ingredients, said capsule being adapted for use in an apparatus that combines a solvent, for example water, and the oral care ingredients to provide a liquid, for example aqueous, oral care composition. The present disclosure also provides apparatus adapted to provide an aqueous oral care composition by directing water through the capsule; aqueous oral care compositions prepared by use of the capsule and/or apparatus, and methods for the use of the aqueous oral care compositions.

12 Claims, 1 Drawing Sheet

(51) Int. Cl.
    *A61K 8/21*     (2006.01)
    *A61K 8/02*     (2006.01)
    *A61K 8/44*     (2006.01)
    *A61K 8/22*     (2006.01)
    *A61K 8/19*     (2006.01)
    *A61Q 11/00*     (2006.01)
    *A61C 9/00*     (2006.01)
    *A61J 3/07*     (2006.01)
    *A61C 19/06*     (2006.01)

(52) U.S. Cl.
    CPC .................. *A61K 8/19* (2013.01); *A61K 8/21* (2013.01); *A61K 8/22* (2013.01); *A61K 8/375* (2013.01); *A61K 8/44* (2013.01); *A61Q 11/00* (2013.01)

(58) Field of Classification Search
    CPC . A61K 8/22; A61K 8/375; A61K 8/44; A61Q 11/00
    USPC ................................ 424/49, 52, 53, 450, 451
    See application file for complete search history.

(56) References Cited

U.S. PATENT DOCUMENTS

| | | | |
|---|---|---|---|
| 3,678,154 A | 7/1972 | Widder et al. | |
| 3,772,431 A | 11/1973 | Mlkvy et al. | |
| 4,487,757 A | 12/1984 | Kiozpeoplou | |
| 4,634,053 A | 1/1987 | Herzfeld et al. | |
| 4,885,155 A | 12/1989 | Parran et al. | |
| 5,392,947 A | 2/1995 | Gentile | |
| 5,648,064 A | 7/1997 | Gaffar et al. | |
| 5,766,674 A | 6/1998 | Hirosawa et al. | |
| 5,840,189 A | 11/1998 | Sylvan et al. | |
| 5,855,871 A | 1/1999 | Masters et al. | |
| 6,082,247 A | 7/2000 | Beaulieu et al. | |
| 6,254,857 B1 | 7/2001 | Hair et al. | |
| 6,333,024 B1 | 12/2001 | Master et al. | |
| 6,606,938 B2 | 8/2003 | Taylor et al. | |
| 6,607,762 B2 | 8/2003 | Lazaris et al. | |
| 6,645,537 B2 | 11/2003 | Sweeney et al. | |
| 7,165,488 B2 | 1/2007 | Bragg et al. | |
| 7,398,726 B2 | 7/2008 | Streeter et al. | |
| 9,161,892 B2* | 10/2015 | Simon | A61K 8/24 |
| 2001/0006624 A1* | 7/2001 | Witt | A61K 8/20 424/53 |
| 2007/0221066 A1 | 9/2007 | Sullivan et al. | |
| 2008/0152768 A1* | 6/2008 | Lan | B65D 85/816 426/125 |
| 2009/0297569 A1* | 12/2009 | Hurwitz | A61K 8/02 424/401 |
| 2010/0322985 A1 | 12/2010 | Kohli et al. | |
| 2012/0121669 A1* | 5/2012 | Fontana | A61K 8/11 424/401 |
| 2013/0032036 A1 | 2/2013 | Zhong et al. | |
| 2013/0032037 A1 | 2/2013 | Zhong et al. | |
| 2013/0149359 A1* | 6/2013 | Sanders | A61Q 11/00 424/401 |
| 2013/0156897 A1 | 6/2013 | Goldstein et al. | |
| 2013/0251861 A1 | 9/2013 | Scapuccin et al. | |
| 2014/0105948 A1* | 4/2014 | Gebreselassie | A61K 8/38 424/401 |
| 2014/0308625 A1 | 10/2014 | Fairley et al. | |
| 2014/0342059 A1 | 11/2014 | Trombetta et al. | |
| 2015/0196469 A1 | 7/2015 | Simon et al. | |
| 2015/0328096 A1 | 11/2015 | Kirkpatrick-Liverman | |
| 2015/0328111 A1 | 11/2015 | Liu et al. | |
| 2015/0328112 A1 | 11/2015 | Xu et al. | |
| 2015/0328118 A1 | 11/2015 | Pan et al. | |
| 2015/0328120 A1 | 11/2015 | Hao et al. | |
| 2015/0335542 A1 | 11/2015 | Pappas et al. | |
| 2016/0193124 A1 | 7/2016 | Porter et al. | |

OTHER PUBLICATIONS

Okamura, 2008, "Portable mouthwashes containing sodium hydrogen," Chemical Abstracts AN: 148:592490CA, JP Patent No. 2006-310404.

JP2008127284, Okamura Mami, "Portable Mouth Rinse," Jun. 5, 2008, English language machine translation of abstract, Espacenet, date obtained: Jan. 23, 2020, 1 page <https://worldwide.espacenet.com/patent/search/family/039553487/publication/JP2008127284A?q=jp2008127284>.

* cited by examiner

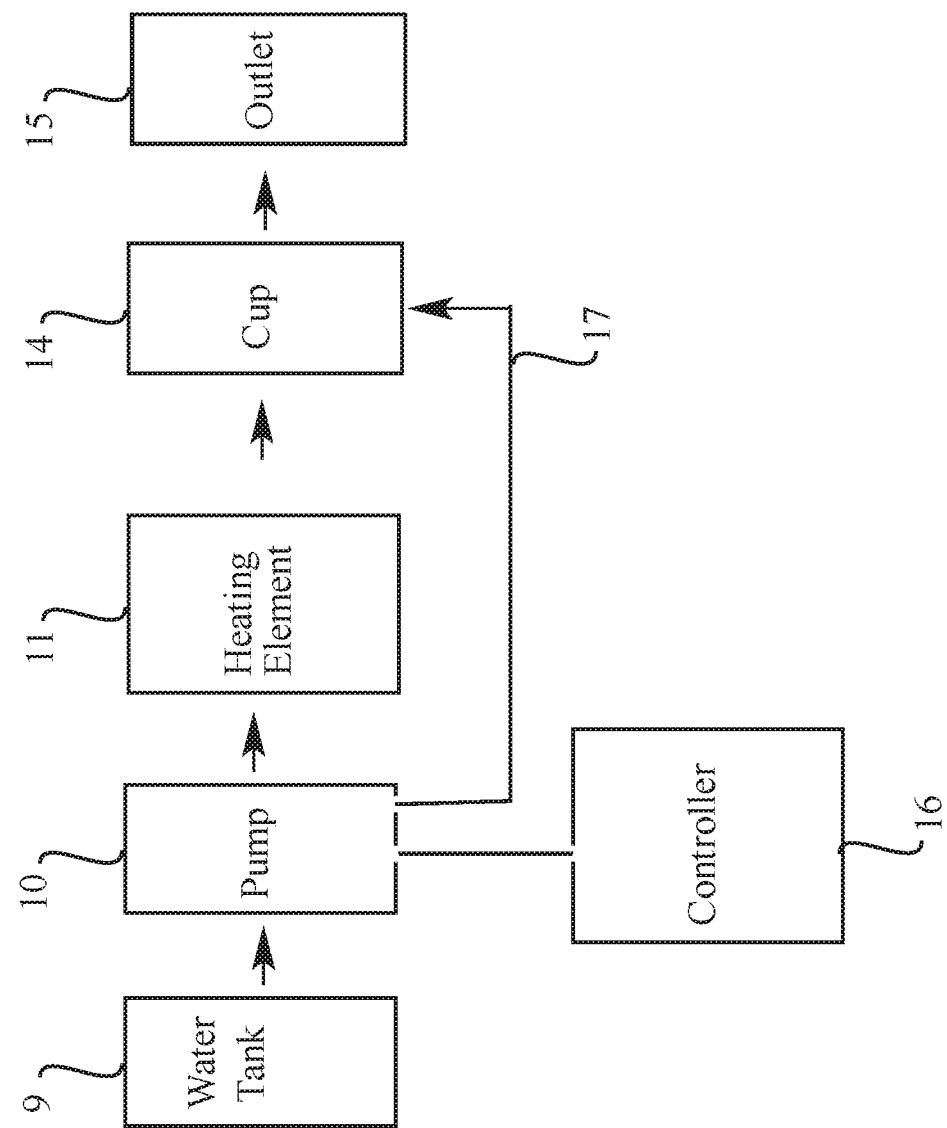

ORAL CARE COMPOSITIONS AND DISPENSING SYSTEM THEREFOR

CROSS-REFERENCE TO RELATED APPLICATIONS

This application claims priority to and the benefit of U.S. Provisional Application No. 62/400,878, filed on Sep. 28, 2016, the contents of which are hereby incorporated by reference in its entirety.

BACKGROUND

There are numerous oral case mouthwash products available for a variety of uses. These products are typically sold as ready-to-use solutions. However, in many instances, more effective formulations are not available because of potential interaction between ingredients when dissolved together and stored for the expected shelf-life of the product. In addition, the consumer has little choice regarding the specific ingredients of commercially available mouthwashes.

It would be desirable to have a system whereby more effective formulations could be provided to the consumer, and the consumer could also have more choice in the mouthwash ingredients.

BRIEF SUMMARY

Compositions, methods of use, apparatus and methods of production for oral care compositions are provided herein.

In one embodiment, the present disclosure provides capsules comprising one or more solid oral care ingredients within a hollow container, wherein the capsules are adapted for use in an apparatus that combines a solvent, e.g. water or an aqueous solution including a solute, and the oral care ingredients to provide a liquid oral care composition, for example, an aqueous oral care composition. The compositions thus provided can be in single dose form, or in multiple dose form, such as a concentrate that can be diluted with water to form the oral care composition, e.g., a mouthwash.

In a further embodiment, the present disclosure also provides apparatus adapted to provide a liquid oral care composition, for example, an aqueous oral care composition, by directing the solvent through the aforementioned capsule.

In a further embodiment, the present disclosure provides a method for preparing an oral mouthwash composition comprising directing a solvent through a capsule according to the present disclosure, whereupon the solvent dissolves at least one of the oral care ingredients in the capsule to form the oral care mouthwash composition.

In a further embodiment, the present disclosure also provides liquid, e.g., aqueous, oral care compositions prepared by use of the capsule and/or apparatus in accordance with the methods described herein.

In a further embodiment, the present disclosure also provides methods for the use of the liquid, e.g., aqueous, oral care compositions.

In a further embodiment, the present disclosure provides a method for one or more of cleansing the teeth and oral cavity; freshening breath; reducing or inhibiting formation of dental caries; reducing erosion; reducing, repairing or inhibiting pre-carious lesions of the enamel, e.g., as detected by quantitative light-induced fluorescence (QLF) or electrical conductance measurement (ECM); reducing or inhibiting demineralization and promote remineralization of the teeth; reducing or inhibiting gingivitis improving oral health; whitening teeth; promoting healing of sores or cuts in the mouth; reducing levels of acid producing bacteria; increasing relative levels of arginolytic bacteria; reducing plaque accumulation; inhibiting microbial biofilm formation in the oral cavity; immunizing the teeth against cariogenic bacteria; reducing the amount of bacteria in an oral cavity; reducing dentinal sensitivity; enhancing systemic health, and/or treating or inhibiting dry mouth, comprising contacting the oral cavity of a patient in need thereof with an oral composition as described herein; or with an oral composition prepared by a method as described herein.

In a further embodiment, the present disclosure provides oral care compositions prepared by the methods described herein.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 1 shows the abridged plan view of an apparatus for use in the practice of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight of the oral care composition after addition of sufficient solvent to provide a single unit dose; i.e., including the solvent, e.g. water or aqueous solution added to the solid ingredients in accordance with the methods described herein. Unless otherwise indicated, the amounts of material given herein are based on the weight of active material.

The present disclosure provides oral care compositions, methods and apparatus for the preparation of the oral care compositions, for example mouthwash compositions. In a first embodiment, the present disclosure provides a capsule (Capsule 1) comprising one or more solid oral care ingredients, wherein the capsules are adapted for use in an apparatus that combines one or more solvents and the oral care ingredients to provide a liquid oral care composition.

The present disclosure provides additional exemplary embodiments, including:

1.1 Capsule 1, wherein the oral care ingredients include or one or more whitening agents such as, for example peroxides, and optionally one or more activators, optionally one or more bases, or optionally one or more activators and one or more bases;

1.2 Capsule 1 or 1.1, wherein the oral care ingredients include or one or more anticalculus agents;

1.3 Capsule 1 or 1.1-1.2, wherein the oral care ingredients include or one or more fluoride sources, for example stannous fluoride, sodium fluoride, potassium fluoride, sodium monofluorophosphate, sodium fluorosilicate, ammonium fluorosilicate, amine fluoride, ammonium fluoride, or combinations thereof;

1.4 Capsule 1 or 1.1-1.3, wherein the oral care ingredients include or one or more antisensitivity agents;

1.5 Capsule 1 or 1.1-1.4, wherein the oral care ingredients include or one or more antibacterial agents;

1.6 Capsule 1 or 1.1-1.5, wherein the oral care ingredients include an acid source and one or more carbonate salts;

1.7 Capsule 1.6, wherein the acid source is selected from citric acid, malic acid, tartaric acid, adipic acid, alginic acid, succinic acid, lactic acid, potassium bitartrate, acid sodium citrate, phosphoric acid, pyrophosphate salts, fumaric acid and mixtures thereof;

1.8 Capsule 1.6 or 1.7, wherein the one or more carbonate salts is selected from sodium bicarbonate, potassium bicarbonate, sodium carbonate, potassium carbonate, arginine bicarbonate, and combinations thereof;

1.9 Capsule 1 or 1.1-1.8, wherein the oral care ingredients include or one or more amino acids such as, for example basic amino acids, for example arginine, lysine, citrullene, ornithine, creatine, histidine, diaminobutanoic acid, diaminoproprionic acid, salts thereof and/or combinations thereof;

1.10 Capsule 1 or 1.1-1.9, wherein the oral care ingredients include or one or more antioxidants;

1.11 Capsule 1 or 1.1-1.10, wherein the oral care ingredients include or one or more breath fresheners, humectants, flavors, preservatives or dyes.

1.12 Capsule 1 or 1.1-1.11, wherein the oral care ingredients are incompatible when stored together in solution.

1.13 Capsule 1 or 1.1-1.12, wherein the oral care composition is a mouthwash.

1.14 Capsule 1 or 1.1-1.13, wherein the one or more oral care ingredients are present in an amount sufficient to provide a single unit dose of the oral care composition.

1.15 Capsule 1 or 1.1-1.13, wherein the one or more oral care ingredients are present in an amount sufficient to provide multiple doses of the oral care composition.

1.16 Capsule 1 or 1.1-1.15, wherein the one or more oral care ingredients comprises a peroxide and a base, or peroxide and an activator, or peroxide and both a base and an activator.

1.17 Capsule 1.16, wherein the peroxide is selected from complexed or uncomplexed hydrogen peroxide and organic peroxides; the base is selected from amino acids, for example basic amino acids, for example arginine and its salts such as arginine bicarbonate, and inorganic hydroxides; and the activator is selected from manganese salts such as manganese gluconate, iron salts such as iron sulfate, copper salts such as copper sulfate, and mixtures thereof.

1.18 Capsule 1 or 1.1-1.17, further comprising additional ingredients selected from analgesic agents, antipyretic agents, anti-inflammatory agents, opioids, and vitamins.

1.19 Capsule 1 or 1.1-1.18 comprising acetylsalicylic acid, ibuprofen, acetaminophen, and medications which are psychotropic, anti-hypertensive, anti-seizure, amphetamine, anti-microbial, antibiotic, anti-viral, anti-retroviral, anti-fungal, anti-depressant, stimulants, anti-histamine, anti-anxiety, tricyclics, tranquilizers, benzodiazepines, hypnotics, mood stabilizers, codeine, selective serotonin reuptake inhibitors, anti-allergy, phenothiazine, chemotherapeutics, amines, monoamine oxidase inhibitors, anti-carcinogens, analgesics, muscle relaxants, ergot preparations, anti-cholinergic, anti-inflammatory, anti-gout preparations, soporific, hormonal preparations, appetite suppressants, analgesics, muscle relaxants, opioids, or combinations of two or more thereof.

1.20 Capsule 1 or 1.1-1.19, wherein the oral care ingredients are in the form of a powder or granulate.

1.21 Capsule 1 or 1.1-1.20, wherein the solvent is water.

1.22 Capsule 1 or 1.1-1.21, wherein the solvent is a mixture comprising water and a humectant, for example a polyhydric alcohol such as glycerin or propylene glycol.

1.23 Capsule 1 or 1.1-1.22, wherein at least one of the solid oral care ingredients in the capsule is sequestered from the other solid ingredients within the capsule.

1.24 Capsule 1 or 1.1-1.23, wherein the capsule has a body generally in the shape of a truncated cone; and is adapted for the introduction of solvent and the egress of solvent together with the oral care ingredients.

In further embodiments, the present disclosure provides an apparatus (Apparatus 1) comprising the following elements:
  at least one tank 9;
  a pump 10;
  at least one one-way water way, fluidly communicating the at least one tank to the pump;
  a capsule cup 14;
  optionally, a seat extractor; and
  optionally, a controller 16, which can vary pumping power of the solvent pump; and
  optionally, a heating element (i.e., boiler 11);
  wherein the apparatus is adapted to provide a liquid, e.g., aqueous, oral care composition;
  and the capsule cup 14 is adapted to contain a capsule according to any of Capsule 1 or 1.1-1.24.

The structure of the waterway of an exemplary apparatus for use in the practice of the invention is shown in FIG. 1: A tank 9, a pump 10, optional heating element 11, and capsule cup 14 are arranged in the shell of the apparatus. The outlet 15 can be the exit port of the capsule cup, or a waterway connection originating therefrom. The short line with arrow in this figure represents the waterway connection and its direction. Water can flow through the heating element and then to the capsule cup, or directly from the tank/pump to the capsule cup via cold route 17. The water tank 9 is used for storing the cold water used for preparing the oral care composition. Water pump 10 runs with certain output power under the seating of the controller 16, so that the cold water entering the optional heating element 11 or proceeding directly to capsule cup 14 via cold route 17 is provide with certain pressure. When employed, heating element 11 is a boiler.

The present disclosure provides additional exemplary embodiments, including:

1.1 Apparatus 1, having substantially the configuration shown in U.S. Patent Application Pub. Nos. 2013/0032037 and/or 2013/0032036.

In further embodiments, the present disclosure provides a Method (Method 1) for preparing an oral care composition, comprising directing a solvent through a capsule according to any of Caspsule 1 or 1.1-1.24, whereupon the solvent dissolves at least one of the oral care ingredients in the capsule to form said oral care composition.

The present disclosure provides additional exemplary embodiments, including:

1.1 Method 1, wherein the solvent is directed through the capsule by use of an apparatus according to any of Apparatus 1, or 1.1;

1.2 Method 1.1, wherein the apparatus contains one tank 1 containing water and another tank 1a containing a humectant; and the solvent is a mixture of the water and the humectant.

In further embodiments, the present disclosure provides a Method (Method 2) for one or more of cleansing the teeth and oral cavity; freshening breath; reducing or inhibiting formation of dental caries; reducing erosion; reducing, repairing or inhibiting pre-carious lesions of the enamel, e.g., as detected by quantitative light-induced fluorescence (QLF) or electrical conductance measurement (ECM); reducing or inhibiting demineralization and promote remineralization of the teeth; reducing or inhibiting gingivitis improving oral health; whitening teeth; promoting healing of sores or cuts in the mouth; reducing levels of acid producing bacteria; increasing relative levels of arginolytic bacteria; reducing plaque accumulation; inhibiting microbial biofilm formation in the oral cavity; immunizing the teeth against cariogenic bacteria; reducing the amount of bacteria in an oral cavity; reducing dentinal sensitivity; enhancing systemic health, and/or treating or inhibiting dry mouth, comprising contacting the oral cavity of a patient in need thereof with an oral care composition prepared by a method as described herein.

In further embodiments, the present disclosure provides an oral care composition prepared by any of Methods 1 or 1.1-1.2.

The present disclosure provides a system whereby, in some embodiments, consumers can prepare oral care compositions from solid ingredients immediately prior to use. The solid ingredients are contained in capsules. The capsules are adapted to fit into an apparatus that directs a solvent stream through the capsule. As the solvent passes through the capsule, at least a portion of the solid ingredients is dissolved in the solvent, which is directed along the solvent-way to an exit point. The product is an oral care composition that is prepared "on demand", and is fresh and ready for use.

In some embodiments, the present disclosure provides "on-demand" methods for preparing oral care compositions from ingredients that are incompatible (i.e., that are unstable or react over the shelf life of the product to produce unacceptable and/or undesired products). Thus, the present disclosure affords the opportunity to provide more effective compositions that were previously not possible to formulate due to undesired interactions between solubilized components of the composition over the shelf life of the composition.

In many instances, providing the ingredients of the oral care compositions in solid form mixed together in a capsule as described herein, is sufficient to avoid the undesirable premature combination of the oral care ingredients. In some embodiments, however, it may be necessary to sequester one or more of the solid oral care ingredients from the others while in the capsule, to ensure that no unacceptable and/or undesired products are formed. In some such embodiments, incompatible oral care ingredients can be sequestered by placement in a separate section or compartment 64 within the capsule. In other embodiments, the incompatible oral care ingredients can be sequestered by combination with additional binders, stabilizing agents and the like to stabilize the solid ingredients and prevent their chemical combination or degradation. Suitable binders are rapidly soluble in solvent, and include, e.g., dextrose, sorbitol, xylitol, and lactose. Preferably, the amount of binder allows for the rapid disintegration upon solvent (e.g., water) introduction into the capsule. In a further embodiment, one or more incompatible solid oral care ingredients can be sequestered in a traditional medicinal capsule, for example a gelatin capsule, that dissolves immediately upon addition of solvent (e.g., water) in accordance with the methods described herein.

In some embodiments of the capsules, methods, apparatuses and compositions of the present disclosure, the solvent is water, and the product of the methods described herein are aqueous oral care compositions, e.g. aqueous mouthwashes. In such embodiments, the first solvent tank of the apparatus of the present disclosure is filled with water.

In some embodiments, it is desirable to add one or more non-water liquid ingredients to the oral care compositions. In such embodiments, the second tank of the apparatus can be filled with the desired liquid component, for example a liquid humectant such as glycerin or propylene glycol or an aqueous solution thereof, and the solvent provided to the capsule is a mixture of the water and the other liquid from the second tank. In such embodiments, the present apparatus includes means to control the relative amounts of the water and second liquid directed into the solvent stream; for example a mixing junction in the solvent way.

Effervescent Compositions:

In some embodiments, the oral care compositions of the present disclosure are effervescent. Effervescence generally results from the reaction of an acid and a soluble carbonate salt in water to produce carbon dioxide. By "soluble carbonate salt" is meant any salt formed by carbonic acid or dissolved carbon dioxide which is sufficiently soluble to react with the acid in the concentrations provided. In aqueous solution, the carbonate ion, bicarbonate ion, carbon dioxide, and carbonic acid form a dynamic equilibrium. The term "carbonate" as used herein thus generally encompasses the bicarbonate ($HCO_3^-$) and carbonate ($CO_3^{2-}$) forms and mixtures thereof, unless otherwise specified. Soluble carbonate salts thus include, e.g., potassium carbonate, potassium bicarbonate, sodium carbonate, and sodium bicarbonate. The acid may, for example, be selected from organic acids such as, without limitation, citric, malic, tartaric, adipic, alginic, succinic, lactic, tartaric, potassium bitartrate, acid sodium citrate, phosphoric acid, pyrophosphate salts and fumaric acid and mixtures thereof. Carbonates include carbonates of amino acids, e.g., basic amino acids, e.g. arginine bicarbonate, as well as alkali carbonates, e.g., such as sodium bicarbonate, potassium bicarbonate, sodium carbonate, and potassium carbonate. Such basic amino acids salts may not only be used as a basic salt, but also impart benefits to the oral cavity. See U.S. Patent Application Pub. No. 2010/0322985, incorporated herein by reference in its entireties for all purposes.

Amino Acids:

In some embodiments, the oral care compositions of the present disclosure include one or more amino acids; for example basic amino acids. Without intending to be bound by a particular theory, it is believed that basic amino acids in the oral cavity are metabolized by certain types of bacteria, e.g., *S. sanguis* which are not cariogenic and which compete with cariogenic bacteria such as *S. mutans*, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities. It is believed that use of a Composition of the Invention may lead to a relative increase in the arginolytic bacteria and a relative decrease in the cariogenic bacteria, resulting in a higher plaque pH.

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine, preferably, arginine, for example, 1-arginine.

In various embodiments, the basic amino acid is present in an amount of about 0.01 wt. % to about 5 wt. % of the total composition weight, about 0.1 wt. % to about 3 wt. % of the total composition weight, for example about 0.5 wt. % to about 1 wt. %, or about 0.75 wt. % of the total composition weight.

The compositions of the invention are used in the mouth, and optionally may be ingested, and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion. A preferred salt is a bicarbonate, e.g., arginine bicarbonate.

Fluoride Ion Source:

The oral care compositions of the present disclosure may optionally include fluoride, or a fluoride ion source e.g., when formulated to be dissolved in a solvent to be used as a mouthwash. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Thus, such effervescence powders may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g. about 1450 ppm. Fluoride ion sources may be added to the compositions of the invention at a level of about 0.01 wt. % to about 10 wt. % in one embodiment or about 0.03 wt. % to about 5 wt. %, and in another embodiment about 0.1 wt. % about 1 wt. % by weight of the composition in another embodiment. Weights of fluoride salts to provide the appropriate level of fluoride ion will obviously vary based on the weight of the counter ion in the salt.

Antibacterial Agents:

The oral care compositions of the present disclosure may also comprise one or more antibacterial agents—i.e., antiseptics and antimicrobial compounds, e.g., herbal extracts and essential oils (e.g., rosemary extract, thymol, menthol, eucalyptol, methyl salicylate), bisguanide antiseptics (e.g., chlorhexidine, alexidine or octenidine), quaternary ammonium compounds (e.g., cetylpyridinium chloride), phenolic antiseptics, hexetidine, povidone iodine, delmopinol, salifluor, metal ions (e.g., zinc salts, for example, zinc citrate), sanguinarine, propolis, and antibiotics. Typically, the antibacterial agent is present in the oral care composition in an antibacterially effective amount, which is typically about 0.01-0.2 wt. %, e.g., 0.01-0.1 wt. %, e.g., about 0.03-0.07 wt. %.

Whitening Agents:

In some embodiments, the solid oral care ingredients include one or more whitening agents. Whitening agents include peroxides (peroxy compounds), alone or together with one or more bases, activators and/or additional whiteners. Suitable peroxy compounds include hydrogen peroxide, peroxides of alkali and alkaline earth metals, organic peroxy compounds and peroxy acids and salts thereof. Any orally acceptable compound that delivers a perhydroxy ($OOH^-$) ion can be used in the present methods and compositions. A peroxy compound can optionally be present in a form of a polymer-peroxide complex, for example a polyvinylpyrrolidone-hydrogen peroxide complex.

Peroxides of alkali and alkaline earth metals include lithium peroxide, potassium peroxide, sodium peroxide, magnesium peroxide, calcium peroxide and barium peroxide.

Organic peroxy compounds include, for example, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and the like.

Peroxy acids and their salts include organic peroxy acids such as alkyl peroxy acids and monoperoxyphthalate, as well as inorganic peroxy acid salts including persulfate, dipersulfate, percarbonate, perphosphate, perborate and persilicate salts of alkali and alkaline earth metals such as lithium, potassium, sodium, magnesium, calcium and barium. Another useful peroxy compound is sodium pyrophosphate peroxyhydrate.

Typically, the peroxide will be present in the oral care composition in an amount sufficient to provide from about 0.05% to about 5% active peroxide; for example 0.1%, 0.5%, 1%, 1.5%, 2%, 2.5%. 3%, 3.5%, 4%, 4.5% or 5% active peroxide.

Additional whitening agents include chlorine dioxide, chlorites and hypochlorites (e.g., chlorites and hypochlorites of alkali and alkaline earth metals such as lithium, potassium, sodium, magnesium, calcium and barium).

Activators:

In some embodiments, the solid oral care ingredients include one or more activators. Activators are compounds that, when combined with the peroxide, function to accelerate the breakdown and rapid release of active oxygen from the peroxide compound, such rapid release being effective for whitening teeth and instilling in the consumer a perception of enhanced product performance. Activators include manganese salts, e.g. manganese gluconate as described in U.S. Pat. No. 5,648,064, and iron and copper salts as described in U.S. Pat. No. 6,254,957, the disclosures of each of which are incorporated herein by reference in their entireties for all purposes. Activators are typically present in the compositions of the present invention in amounts of between about 0.001% and about 3% by weight of the composition.

When present in the compositions of the present invention, iron and copper salt activators respectively are at a weight ratio of 0.5:2.0 to 2.0 to 0.5 and preferably 1:1, such ratio being dependent upon the amount of peroxide compound in the composition. Typically, when present in the compositions of the present disclosure, the iron and copper salt mixture is present in an amount of between about 0.01% and about 3% by weight of the composition, for example between about 0.01% and about 2% by weight, for example between about 0.01% and about 1% by weight, for example between about 0.01% and about 0.5% by weight of the composition.

The solid oral care compositions can include one or more tartar control (anticalculus) agents. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Tartar control agents are typically present in the oral care compositions of the present disclosure at a concentration of from about 0.01 to about 3% by weight.

Anticalculus Agents:

In some embodiments, the solid oral care ingredients include an anticalculus-effective amount of one or more pyrophosphate salts, e.g., selected from dialkali or tetraalkali metal pyrophosphate salts, e.g. $Na_4P_2O_7$ (tetrasodium pyrophosphate or TSPP), $K_4P_2O_7$ (tetrapotassium pyrophosphate or TKPP), $Na_2K_2P_2O_7$, $Na_2H_2P_2O_7$ and $K_2H_2P_2O_7$ and combinations thereof, for example, in a total amount of 0.5-5%, e.g., 1-3%. In some embodiments, the solid oral care ingredients include a combination of TSPP and TKPP, e.g., in a total amount of 1-3%, e.g., in a ratio of from 1:1 to 1:5, for example comprising in one embodiment about 0.3-0.6%, e.g., 0.4-0.5% of TSPP and 1.2-1.5%, e.g. 1.3-1.4% of TKPP.

Flavoring Agents:

In some embodiments, the oral care ingredients can include one or more flavoring agents. Flavoring agents are known, such as natural and artificial flavors. These flavorings may be chosen from essential oils as well as various flavoring aldehydes, esters, alcohols, and similar materials, synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, oil of bitter almonds, and oils of wintergreen, sassafras, clove, sage, eucalyptus, marjoram, cinnamon, lemon, lime, grapefruit, and orange. Also useful are such chemicals as menthol, carvone, and anethole. Further commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63-258, may be used.

These flavor agents can be used individually or in admixture. Typically, flavorants if included are present at 0.001-5%, by weight; for example about 0.01-1% by weight; for example about 0.1-1% by weight.

Desensitizing Agents:

In some embodiments, the oral care ingredients can include one or more desensitizing agents, for example potassium and strontium salts. Suitable potassium salts include the nitrate, chloride, bromide, iodide, citrate, acetate, lactate, tartrate, bicarbonate, oxalate and hydrogen carbonate. Typically, the potassium salt will be present in a range to provide from 0.01 to 5%, preferably 0.05 to 3% by weight of the composition as potassium ions. Suitable strontium salts include the chloride, bromide, iodide, acetate, edetate, nitrate, salicylate and lactate. Typically, the strontium salt is present in a range to provide from 0.01 to 5%, preferably 0.05 to 3% weight of the composition as strontium ions. In some embodiments, a local or systemic analgesic such as aspirin, codeine, acetaminophen, sodium salicylate or triethanolamine salicylate can be used, typically an amount from about 0.01% to about 7.5% by weight.

Other Actives:

The oral care compositions of the present disclosure may also include one or more medicaments or other active, e.g., acetylsalicylic acid, acetaminophen, vitamins, and medications which are psychotropic, anti-hypertensive, anti-seizure, amphetamine, anti-microbial, antibiotic, anti-viral, anti-retroviral, anti-fungal, anti-depressant, stimulants, antihistamine, anti-anxiety, tricyclics, tranquilizers, benzodiazepines, hypnotics, mood stabilizers, codeine, selective serotonin reuptake inhibitors, anti-allergy, phenothiazine, chemotherapeutics, amines, monoamine oxidase inhibitors, anti-carcinogens, analgesics, muscle relaxants, ergot preparations, anti-cholinergic, anti-inflammatory, anti-gout preparations, soporific, hormonal preparations, appetite suppressants, analgesics, muscle relaxants, and opioids. Such medicaments or other active can be present in any effective amount, for example from about 0.01% to about 5% by weight; for example from about 0.05% to about 2% by weight.

In some embodiments, the oral care ingredients can include one or more breath freshening agents. Any orally acceptable breath freshening agent can be used, including without limitation zinc salts such as zinc gluconate, zinc citrate and zinc chlorite, alpha-ionone and mixtures thereof. One or more breath freshening agents are optionally present in a breath freshening effective total amount.

In some embodiments, the oral care ingredients can include one or more antioxidants. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In some embodiments, the oral care ingredients can include one or more saliva stimulating agents, useful for example in amelioration of dry mouth. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

In some embodiments, the oral care ingredients can include one or more antiplaque (e.g., plaque disrupting) agents. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

In some embodiments, the oral care ingredients can include additional ingredients selected from analgesic agents, antipyretic agents, anti-inflammatory agents, opioids, and vitamins. Representative examples of the foregoing include acetylsalicylic acid, ibuprofen, acetaminophen, and medications which are psychotropic, anti-hypertensive, anti-seizure, amphetamine, anti-microbial, antibiotic, anti-viral, anti-retroviral, anti-fungal, anti-depressant, stimulants, anti-histamine, anti-anxiety, tricyclics, tranquilizers, benzodiazepines, hypnotics, mood stabilizers, codeine, selective serotonin reuptake inhibitors, anti-allergy, phenothiazine, chemotherapeutics, amines, monoamine oxidase inhibitors, anti-carcinogens, analgesics, muscle relaxants, ergot preparations, anti-cholinergic, anti-inflammatory, anti-gout preparations, soporific, hormonal preparations, appetite suppressants, analgesics, muscle relaxants, opioids, and combinations thereof.

Humectants:

In some embodiments, the oral care ingredients can include a humectant, e.g., a polyhydric alcohol such as sorbitol. Humectants useful herein include polyhydric alcohols that are solids at ambient temperature, such as sorbitol, xylitol or and low molecular weight polyethylene glycols (PEGs). In some embodiments, the humectant is present in the amount of about 1 to about 40% each by weight. In some embodiments, the humectant is sorbitol. In some embodiments sorbitol present at a concentration of from about 5 to about 25%, by weight. In some embodiments sorbitol present at a concentration of from about 5 to about 15%, by weight. In some embodiments, the sorbitol is present at a concentration of about 7-10%, by weight. Reference to sorbitol herein are adjusted to refer to the material by dry weight, although the material is typically as available commercially in 70% aqueous solutions. Preferably, the humectant, e.g. sorbitol, is included in the capsule as a dry powder. In some embodiments, the total humectant concentration is from about 1 to about 60%, by weight.

Preservatives:

In some embodiments, the oral care ingredients can include a preservative. In some embodiments, the preservative is selected from parabens, potassium sorbate, benzyl alcohol, phenoxyethanol, polyaminopropryl biguanide, caprylic acid, sodium benzoate and cetylpyridinium chloride, some of which can also act as antibacterial agents. In some embodiments, the preservative is present at a concentration of from about 0.0001 to about 1%, by weight. In some embodiments, the preservative is present at a concentration of from about 0.01 to about 1%, by weight. In some embodiments, the preservative is present at a concentration of about 0.5%, by weight.

Sweeteners:

In some embodiments, the oral care ingredients can include one or more sweeteners. Sweeteners include both natural and artificial sweeteners. Suitable sweetener include, but are not limited to water soluble saccharide sweetening agents such as monosaccharides, disaccharides and polysaccharides such as xylose, ribose, glucose (dextrose), mannose, galactose, fructose (levulose), sucrose (sugar), maltose, and water soluble artificial non-saccharide sweeteners such as the soluble saccharin salts, i.e., sodium or calcium saccharin salts, cyclamate salts dipeptide based sweeteners, such a L-aspartic acid derived sweeteners, such as L-aspartyl-L-phenylalanine methyl ester (aspartame). In general, the effective amount of sweetener is utilized to provide the level of sweetness desired for a particular composition, will vary with the sweetener selected. This amount will normally be about 0.001% to about 5% by weight of the composition. In some embodiments, the sweetener is a combination of sucralose present at 0.001-0.003% and sodium saccharin present at about 0.01-0.03% by weight of the composition.

Polymers:

In some embodiments, the oral care ingredients can include one or more PVM/MA copolymers. "PVM/MA copolymer" as used herein is intended to include copolymers of maleic anhydride or acid with another polymerizable ethylenically unsaturated monomer, for example methyl vinyl ether/maleic anhydride. In some embodiments, the copolymers include 1:4 to 4:1 copolymers of maleic anhydride or acid with another polymerizable ethylenically unsaturated monomer, e.g., methyl vinyl ether (methoxyethylene), having a molecular weight (M.W.) of about 30,000 to about 2,500,000; for example 1:4 to 4:1, e.g. about 1:1, copolymers of methyl vinyl ether/maleic anhydride, wherein the anhydride is hydrolyzed following co-polymerization to provide the corresponding acid, having a molecular weight (M.W.) of about 30,000 to about 1,000,000, e.g. about 300,000 to about 800,000, e.g., as sold under the trade name GANTREZ®. Representative useful GANTREZ® copolymers include, e.g., GANTREZ® S polymers, for example GANTREZ® S-96 Pharmaceutical Grade and GANTREZ® S-97BF Pharmaceutical Grade available from Ashland Specialty Chemicals, Bound Brook, N.J. 08805. In some embodiments, the PVM/MA copolymer is present in the oral care compositions of the disclosure in an amount of from 0.01% to 2%, for example from 0.01% to 1%, for example from 0.03% to 1%, for example from 0.05% to 0.08%, for example from 0.06% to 0.07%, by weight of the composition.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinyl acetate, vinyl chloride, dimethyl maleate and the like. Copolymers may contain sufficient carboxylic salt groups for water-solubility.

Surfactants:

In some embodiments, the oral care ingredients can include one or more surfactants, for example anionic surfactants, zwitterionic surfactants or nonionic surfactants. In some embodiments, the surfactants can comprise from 0.01% to 3%, for example from 0.01% to 2%, for example from 0.05% to 1% of the composition by weight. Representative anionic surfactants include the water-soluble salts of alkyl sulfates and sulfonates, and alkyl ether sulfates and sulfonates having from 8 to 20 carbon atoms in the alkyl radical (e.g., sodium alkyl sulfate) and the water-soluble salts of sulfonated monoglycerides of fatty acids having from 8 to 20 carbon atoms. Sodium laurel ether sulfate (SLES; sodium laureth sulfate), sodium lauryl sulfate and sodium coconut monoglyceride sulfonates are examples of anionic surfactants of this type. Examples of nonionic surfactants that can be used in the present compositions include polysorbates, e.g. polysorbate 20. Further examples of suitable nonionic surfactants include poloxamers (sold under trade name PLURONIC®), for example Poloxamers 335 and 407. The surfactant will typically be present in from 0.01 to 2%, for example 0.05 to 1% by weight of the composition.

In some embodiments, the oral care ingredients can include one or more dyes. Such dyes are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-N-ethyl-N-p-sulfobenzyl)-3,5-cyclohexadienimine], FD&C Blue No. 1 (disodium salt of dibenzyldiethyldiaminotriphenylcarbinol trisulfonic acid anhydride), FD&C Blue No. 2 (sodium salt of disulfonic acid of indigotin) and mixtures thereof in various proportions. The concentration of the dye for the most effective result in the present invention is present in the composition in an amount from about 0.0005 percent to about 2 percent by weight.

Representative mouthwash compositions suitable for use in the present invention include those that are described in the following publications, the disclosures of each of which are incorporated herein by reference in their entireties for all purposes: U.S. Patent Publication No. 2015/1096469, U.S. Patent Publication No. 2015/0328096; U.S. Patent Publication No. 2015/0328111; U.S. Patent Publication No. 2015/0328112; U.S. Patent Publication No. 2015/0328118; U.S. Patent Publication No. 2015/0328120; U.S. Patent Publication No. 2015/0335542; U.S. Patent Publication No. 2010/0322985; U.S. Pat. Nos. 5,766,674; 5,648,064; 6,254,857; U.S. Patent Application Pub. No. 2010/0322985; U.S. Pat. No. 9,161,892.

It is understood that while general attributes of each of the above categories of materials may differ; there may be some common attributes, and any given material may serve multiple purposes within two or more categories of materials.

The apparatus can be of any configuration, provided only that the solvent stream is directed through the capsule whereupon it is mixed with the contents of the capsule, and then directed out of the apparatus for collection by a vessel, e.g., a cup or glass in the case of a single dose, or a larger vessel in embodiments where the capsule contains an amount of solid ingredients sufficient to make multiple doses. Representative apparatuses and capsules that are amenable to the present methods include those manufactured by Nespresso, Keurig and the like, and are disclosed in, for example, U.S. Pat. Nos. 5,840,189; 6,082,247; 6,606,938; 6,607,762; 6,645,537, 7,398,726; 7,165,488; and 7,398,726; and more preferably in U.S. Patent Application Pub. Nos. 2013/0032037, and 2013/0032036, the disclosures of which are incorporated herein by reference in their entireties for all purposes.

In some embodiments, the amount of solid ingredients can be sufficient to make any convenient amount, for a liter, of oral care composition. In some such embodiments, the product of the apparatus is a concentrate, that can be dispensed into a vessel, to which the end user can then add additional solvent, e.g. water, to make the working solution. Alternatively, the apparatus can dispense the whole amount of solvent to make the working solution.

In some embodiments, the capsules are encoded with machine-readable signals that identify the contents of the capsule and direct the use of pre-programmed amount of solvent, temperature, and solvent flow rate. Such machine-readable signals are commonly used in apparatuses manufactured by Nespresso, Keurig and the like, and are disclosed in the publications listed above.

EXAMPLES

Exemplary embodiments of the present disclosure will be illustrated by reference to the following examples, which are included to exemplify, but not to limit the scope of the present invention.

In the examples and elsewhere in the description of the invention, chemical symbols and terminology have their usual and customary meanings. Temperatures are in degrees Celsius unless otherwise indicated. Unless otherwise indicated, the amounts of the components are in weight percent based on the weight of active ingredient. Various names of chemical components include those listed in the CTFA International Cosmetic Ingredient Dictionary (Cosmetics, Toiletry and Fragrance Association, Inc., $7^{th}$ ed. 1997).

Example 1—Preparation of Capsules with Effervescent Mouthwash Compositions

Powder compositions are formulated containing:
a) 50 wt. % Arginine bicarbonate and 50 wt. % Citric Acid;
b) 40 wt. % Arginine bicarbonate, 50 wt. % Citric Acid, 10 wt. % sodium bicarbonate;
c) 10 grams of composition (a) and 0.5 grams of acetylsalicylic acid;
d) 10 grams of composition (b) and 0.5 grams of acetylsalicylic acid.

The compositions are placed into capsules and sealed with foil to effect an air-tight seal.

Example 2—Preparation of Effervescent Mouthwash Compositions

The capsules from Example 1 are placed into an apparatus having a tank containing water; a water pump; a controller which can vary the pumping power of the water pump; a capsule seat; tubing connecting the aforementioned components, and other components as disclosed in U.S. Patent Application Publication No. 2013/0032037 or 2013/0032036, which disclosures are both hereby incorporated by reference herein as if set forth in their entirety. The apparatus is configured so as to not engage the boiler. The apparatus is engaged, and water flows from the water tank through the tubing (water way) to the capsule whereupon it enters the capsule and moves through the capsule, where it mixes with the contents of the capsule to form the oral care composition, which is then is directed out of the capsule along the water way and out of the apparatus. The oral care composition is collected in a vessel, e.g., a cup or glass, and is ready for use.

Example 3—Preparation of Effervescent Mouthwash Compositions

The oral care compositions of Example 2 are prepared as described in Example 2, using the apparatus as disclosed in U.S. Patent Application Publication No. 2013/0032037 or 2013/0032036, modified so as to not engage the boiler.

Example 4—Preparation of Other Mouthwash Compositions

The oral care compositions a-f are prepared as described in Examples 1-3, having the following actives:
a) 0.5-5 wt % hydrogen peroxide whitening agent;
b) 3 wt % of a 1:1 w:w mixture of TSPP and TKPP;
c) (a) or (b) above and sodium fluoride in an amount sufficient to provide about 1450 ppm fluoride ions;
d) (a), (b) or (c) above and 2 wt % potassium nitrate;
e) (a)-(d) above and 0.07 wt % cetylpyridinium chloride;
f) (a)-(e) above and 7% 1-arginine or 1-arginine bicarbonate.

What is claimed is:

1. A capsule comprising a mixture of solid oral care ingredients within a hollow container, said capsule being adapted for use in an apparatus that combines a solvent, wherein said solvent is water, and said mixture of solid oral care ingredients to provide a mouthwash composition;
wherein the mixture of solid oral care ingredients comprise
a) complexed or uncomplexed hydrogen peroxide;
b) arginine bicarbonate; and
c) an active selected from the group consisting of tetrasodium pyrophosphate, sodium fluoride, tetrapotassium pyrophosphate, potassium nitrate, cetylpyridinium chloride, and an acid source which is selected from the group consisting of citric acid, malic acid, tartaric acid, adipic acid, alginic acid, succinic acid, lactic acid, potassium bitartrate, acid sodium citrate, phosphoric acid, pyrophosphate salts, fumaric acid and mixtures thereof;
wherein the mixture of solid oral care ingredients are incompatible when stored together in solution.

2. The capsule of claim 1, wherein said mixture of solid oral care ingredients are present in an amount sufficient to provide a single unit dose of said oral care composition.

3. The capsule of claim 1, wherein said mixture of solid oral care ingredients are present in an amount sufficient to provide multiple doses of said oral care composition.

4. The capsule of claim 1, wherein said mixture of solid oral care ingredients further comprises one or more additional ingredients selected from the group consisting of analgesic agents, antipyretic agents, anti-inflammatory agents, opioids, and vitamins.

5. The capsule of any preceding claim 1, wherein said mixture of solid oral care ingredients further comprises one or more additional ingredients selected from the group consisting of ibuprofen, acetaminophen, and medications which are psychotropic, anti-hypersensitive, anti-seizure, amphetamine, antimicrobial, antibiotic, anti-viral, anti-retroviral, anti-fungal, anti-depressant, stimulants, anti-histamine, anti-anxiety, tricyclics, tranquilizers, benzodiazepines, hypnotics, mood stabilizers, codeine, selective serotonin reuptake inhibitors, antiallergy, phenothiazine, chemotherapeutics, amines, monoamine oxidase inhibitors, anti-carcinogens, analgesics, muscle relaxants, ergot preparations, anticholinergic, anti-inflammatory, anti-gout preparations, soporific, hormonal preparations, appetite suppressants, analgesics, muscle relaxants, opioids, and combinations thereof.

6. The capsule of claim 1, wherein said oral care ingredients are in the form of a powder or granulate.

7. The capsule of claim 1, wherein said solvent is a mixture comprising water and a humectant, wherein said humectant is glycerin or propylene glycol.

8. The capsule of claim 1, wherein at least one of the solid oral care ingredients in the capsule is sequestered from the other solid ingredients within the capsule.

9. The capsule of claim 1, wherein said container:
a) is in the shape of a truncated cone; and
b) is adapted for the introduction of solvent and the egress of solvent together with the oral care ingredients.

10. A method for preparing an oral care composition, comprising directing a solvent through the capsule according claim 1; whereupon the solvent dissolves at least one of said oral care ingredients in said capsule to form said oral care composition.

11. A method for one or more of:
a) cleansing the teeth and oral cavity;
b) freshening breath;
c) reducing formation of dental caries;
d) reducing erosion;
e) reducing or repairing pre-carious lesions of the enamel, e.g., as detected by quantitative light-induced fluorescence (QLF) or electrical conductance measurement (ECM);
f) reducing demineralization and promote remineralization of the teeth;
g) reducing gingivitis
h) improving oral health;
i) whitening teeth;
j) promoting healing of sores or cuts in the mouth;
k) reducing levels of acid producing bacteria;
l) increasing relative levels of arginolytic bacteria;
m) reducing plaque accumulation;
n) reducing microbial biofilm formation in the oral cavity;
o) immunizing the teeth against cariogenic bacteria;
p) reducing the amount of bacteria in an oral cavity;
q) reducing dentinal sensitivity;
r) enhancing systemic health, and/or
s) treating dry mouth;
comprising contacting an oral cavity of a patient in need thereof with the oral composition prepared by the method of a claim 10.

12. An oral care composition prepared by the method of claim 10.

* * * * *